United States Patent [19]
Demerson et al.

[11] 4,100,277
[45] Jul. 11, 1978

[54] 4,1-BENZOXAZONINE DERIVATIVES AND PROCESS THEREFOR

[75] Inventors: Christopher A. Demerson, Montreal; Leslie G. Humber, Dollard des Ormeaux, both of Canada

[73] Assignee: American Home Products Corporation, New York, N.Y.

[21] Appl. No.: 739,778

[22] Filed: Nov. 8, 1976

[51] Int. Cl.² .................. C07D 267/00; A61K 31/33
[52] U.S. Cl. ........................... 424/244; 260/239.3 B; 260/333; 260/326.5 B
[58] Field of Search ................ 260/239.3 B, 333 R; 424/244

[56] References Cited
U.S. PATENT DOCUMENTS
3,830,803   8/1974   Klohs et al. .................. 260/239.3 B OTHER PUBLICATIONS
Gabriel "Berichte" vol. 38, pp. 2389–2414 (1905).

Primary Examiner—Henry R. Jiles
Assistant Examiner—Robert T. Bond
Attorney, Agent, or Firm—Adley F. Mandel

[57] ABSTRACT

4,1-Benzoxazonine derivatives characterized by having an alkyl radical at the 3-position as well as being further substituted at the 3-position are disclosed. The derivatives are optionally further substituted at positions 1,2,6 and 7. The 4,1-benzoxazine derivatives of this invention are useful for treating hypertension and microbial infections. Methods for the preparation and use of these derivatives are described.

31 Claims, No Drawings

4,1-BENZOXAZONINE DERIVATIVES AND PROCESS THEREFOR

BACKGROUND OF THE INVENTION

1. Field of the Invention

This invention relates to novel 4,1-benzoxazonine derivatives, to processes for their preparation, to methods for using the 4,1-benzoxazonine derivatives and to pharmaceutically acceptable compositions of said derivatives.

More specifically, the present invention relates to novel 4,1-benzoxazonine derivatives possessing valuable pharmacologic properties. For example, these derivatives are useful for treating hypertension and microbial infections in a mammal at dosages which do not elicit undesirable side effects. The combination of these pharmacologic properties together with a low order of toxicity render the 4,1-benzoxazonine derivatives of the invention therapeutically useful.

2. Description of the Prior Art

Only a rather limited number of reports dealing with benzoxazonines are available. A typical report describes substituted 1,3,4,5,6,7-hexahydro-2,6-benzoxazonines, see U.S. Pat. No. 3,830,803, Aug. 20, 1974. Other classes of benzoxazonines have also been reported, for example, 1-aza-8,9-benzocyclononen-2,7-diones, described by L. J. Dolby and D. L. Booth, J. Amer. Chem. Soc., 88, 1049(1966). The compounds of the present invention are distinguished from the prior art compounds by possessing the novel 4,1-benzoxazonine nucleus.

SUMMARY OF THE INVENTION

The compounds of this invention are represented by formula I

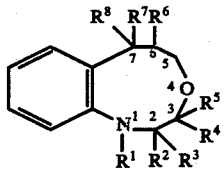

in which $R^1$ is hydrogen, $CO(CH_2)_n NR^9 R^{10}$ wherein n is an integer from 1 to 4 and $R^9$ and $R^{10}$ each is hydrogen or lower alkyl, or $CH_2(CH_2)_n NR^9 R^{10}$ wherein n, $R^9$ and $R^{10}$ are as defined herein; $R^2$ is hydrogen; $R^3$ is hydrogen; or $R^2$ and $R^3$ together are oxo; $R^4$ is lower alkyl; $R^5$ is lower alkyl or $(CH_2)_p Y$ wherein p is an integer from 1 to 5 and Y is halo, lower alkoxycarbonyl or $CONR^{11}R^{12}$ wherein $R^{11}$ and $R^{12}$ each is hydrogen or lower alkyl; $R^6$ is hydrogen or lower alkyl; and $R^7$ is hydrogen and $R^8$ is amino; or $R^7$ is hydroxy and $R^8$ is hydrogen, lower alkyl or phenyl; or $R^7$ and $R^8$ together are oxo, with the proviso that when $R^2$ and $R^3$ together are oxo and $R^4$, $R^5$, $R^6$, $R^7$ and $R^8$ are as defined herein then $R^1$ is hydrogen; and with the additional proviso that when $R^2$ and $R^3$ are hydrogen and $R^1$, $R^4$ and $R^6$ are as defined herein then $R^5$ is lower alkyl; $R^7$ is hydroxy; and $R^8$ is hydrogen, lower alkyl or phenyl.

One preferred group of compounds of formula I are those in which $R^1$ is hydrogen; $R^2$ and $R^3$ are oxo; $R^4$ is lower alkyl; $R^5$ is lower alkyl, $(CH_2)_p Y$ wherein p is an integer from 1 to 5 and Y is halo, lower alkoxycarbonyl or $CONR^{11}R^{12}$ wherein $R^{11}$ and $R^{12}$ each is hydrogen or lower alkyl; $R^6$ is hydrogen or lower alkyl; $R^7$ is hydrogen; and $R^8$ is amino; or $R^7$ is hydroxy and $R^8$ is hydrogen, lower alkyl or phenyl; or $R^7$ and $R^8$ together are oxo.

Another preferred group of compounds of formula I are those in which $R^1$ is hydrogen, $CO(CH_2)_n NR^9 R^{10}$ wherein n is an integer from 1 to 4, $R^9$ and $R^{10}$ each is hydrogen or lower alkyl, or $CH_2(CH_2)_n NR^9 R^{10}$ wherein n is an integer from 1 to 4, $R^9$ and $R^{10}$ each is hydrogen or lower alkyl; $R^2$ is hydrogen; $R^3$ is hydrogen; $R^4$ is lower alkyl; $R^5$ is lower alkyl; $R^6$ is hydrogen or lower alkyl; $R^7$ is hydroxy; and $R^8$ is hydrogen, lower alkyl or phenyl.

Also included are the therapeutically acceptable acid addition salts of the basic compounds of formula I The 4,1-benzoxazonine derivatives of this invention of formula I are prepared by oxidizing a compound of formula II

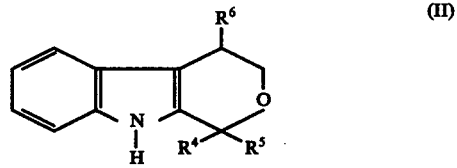

in which $R^4$, $R^5$ and $R^6$ are as defined herein to obtain the corresponding compound of formula V

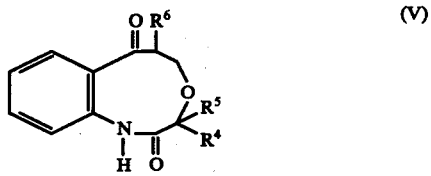

in which $R^4$, $R^5$ and $R^6$ are as defined herein; followed when said compound of formula V is different from said compound of formula I, by transformation of said compound of formula V to said compound of formula I by methods described herein.

More specifically, the transformation of said compound of formula V to said compound of formula I comprises:

a. reducing said compound of formula V in which $R^4$, $R^5$ and $R^6$ are as defined herein with hydrogen in the presence of a noble metal catalyst or a suitable complex borohydride to obtain the corresponding compound of formula I in which $R^4$, $R^5$ and $R^6$ are as defined herein, $R^1$ is hydrogen, $R^2$ and $R^3$ together are oxo, and $R^7$ is hydroxy and $R^8$ is hydrogen; or b. reacting said compound of formula V in which $R^4$, $R^5$ and $R^6$ are as defined herein with hydroxylamine to obtain the corresponding oxime, followed by reduction of the latter oxime by hydrogen in the presence of a noble metal catalyst to obtain the corresponding compound of formula I in which $R^4$, $R^5$ and $R^6$ are as defined herein, $R^1$ is hydrogen, $R^2$ and $R^3$ together are oxo, $R^7$ is hydrogen and $R^8$ is amino; or c. reacting said compound of formula V in which $R^4$, $R^5$ and $R^6$ are as defined herein with a lower alkyl or phenyl magnesium halide wherein the halogen is selected from chlorine, bromine or iodine to obtain the corresponding compound of formula I in which $R^4$, $R^5$ and $R^6$ are as defined herein, $R^1$ is hydrogen, $R^2$ and $R^3$ together are oxo, $R^7$ is hydroxy and $R^8$ is lower alkyl or phenyl; or d. reducing the latter compound of formula I in which $R^1$, $R^2$, $R^3$, $R^4$, $R^6$, $R^7$ and $R^8$ are as defined immediately above and $R^5$ is lower alkyl with a suitable complex metal hydride to obtain the corresponding compound of formula I in which $R^1$, $R^2$ and $R^3$ are hydrogen; $R^4$, and $R^6$ are as defined herein; $R^5$ is lower alkyl; $R^7$ is hydrogen and $R^8$ is lower alkyl or phenyl; and if desired, reacting said last-named compound of formula I with a halo(lower) alkanoyl halide of formula (Halogen)-CO(CH$_2$)$_n$-(Halogen) wherein n is an integer from 1 to 4 and the halogens are selected from bromine, iodine or chlorine to a corresponding haloalkanoylate intermediate of formula I in which $R^1$ is CO(CH$_2$)$_n$-Halogen, followed by amination of the latter compound with an amine of formula HNR$^9$R$^{10}$ in which $R^9$ and $R^{10}$ are as defined herein to obtain the corresponding compound of formula I in which $R^1$ is CO(CH$_2$)$_n$NR$^9$R$^{10}$ wherein n, $R^9$ and $R^{10}$ are as defined herein, $R^2$ and $R^3$ are hydrogen, $R^4$ and $R^6$ are as defined herein; $R^5$ is lower alkyl; $R^7$ is hydroxy and $R^8$ is lower alkyl or phenyl; and if desired, reducing said last-named compound of formula I with a suitable complex metal hydride to obtain the corresponding compound of formula I in which $R^1$ is CH$_2$(CH$_2$)$_n$NR$^9$R$^{10}$ wherein n, $R^9$ and $R^{10}$ are as defined herein, $R^2$ and $R^3$ are hydrogen; $R^4$ and $R^6$ are as defined herein; $R^5$ is lower alkyl; $R^7$ is hydroxy and $R^8$ is lower alkyl or phenyl; or e. reducing said compound of formula V in which $R^4$ and $R^6$ are as defined herein, and $R^5$ is lower alkyl with a suitable complex metal hydride to obtain the corresponding compound of formula I in which $R^4$ and $R^6$ are as defined herein, $R^1$, $R^2$, $R^3$ and $R^8$ are hydrogen, $R^5$ is lower alkyl and $R^7$ is hydroxy; and if desired, reacting said last-named compound of formula I with a halo(lower)alkanoyl halide of formula (Halogen)-CO(CH$_2$)$_n$-(Halogen) wherein n is an integer from 1 to 4 and the halogens are selected from bromine, iodine or chlorine to a corresponding haloalkanoylate intermediate of formula I in which $R^1$ is CO(CH$_2$)$_n$-Halogen, followed by amination of the latter compound with an amine of formula HNR$^9$R$^{10}$ in which $R^9$ and $R^{10}$ are as defined herein and $R^2$, $R^3$ and $R^8$ are hydrogen, $R^4$ and $R^6$ are as defined herein, $R^5$ is lower alkyl and $R^7$ is hydroxy; and if desired, reducing said last-named compound of formula I with a suitable complex metal hydride to obtain the corresponding compound of formula I in which $R^1$ is CH$_2$(CH$_2$)$_n$NR$^9$R$^{10}$ wherein n, $R^9$ and $R^{10}$ are as defined herein, $R^2$, $R^3$ and $R^8$ are hydrogen, $R^4$ and $R^6$ are as defined herein, $R^5$ is lower alkyl and $R^7$ is hydroxy.

Another aspect of this invention involves a method for treating hypertension in a mammal which comprises administering to said mammal an effective antihypertension amount of a compound of formula I, or a therapeutically acceptable salt thereof.

Still another aspect involves a method for treating microbial infections in a mammal which comprises administering to said mammal an effective antimicrobial amount of a compound of formula I, or a therapeutically acceptable salt thereof.

Still another aspect involves a pharmaceutical composition comprising a compound of formula I, or a therapeutically acceptable salt thereof, and a pharmaceutically acceptable carrier.

DETAILED DESCRIPTION OF THE INVENTION

The term "lower alkyl" as used herein contemplates straight chain alkyl radicals containing from one to six carbon atoms and branched chain alkyl radicals containing three to four carbon atoms and includes methyl, ethyl, propyl, isopropyl, butyl, isobutyl, pentyl, hexyl and the like.

The term "complex metal hydride" as used herein contemplates the metal hydrides, including lithium aluminum hydride, lithium aluminum hydride-aluminum chloride, aluminum hydride-aluminum chloride, diborane, sodium borohydride-aluminum chloride and the like.

The term "complex borohydride" as used herein contemplates the metal borohydrides, including sodium borohydride, potassium borohydride, lithium borohydride, zinc borohydride and the like, and metal trihydrocarbyl-borohydrides including lithium 9-alkyl-9-borabicyclo[3,3,1]-nonylhydride, in which the alkyl contains one to seven carbon atoms, preferably lithium 9-tert-butyl-9-borabicyclo[3,3,1]nonylhydride, prepared according to the procedure described in German Offenlegungsschrift 2,207,987, published Aug. 31, 1972, lithium diisopinocamphenyl-tert-butylborohydride and lithium 2-thexyl-4,8-dimethyl-2-borobicyclo[3,3,1]nonylhydride, described by E. J. Corey et al., J. Amer. Chem. Soc., 93, 1491 (1971), lithium perhydro-9b-borophenalylhydride, described by H. C. Brown and W. C. Dickason, J. Amer. Chem. Soc., 92, 709 (1970) and the like.

The terms "halo" and "halide" as used herein contemplates halogens and includes fluorine, chlorine, bromine and iodine unless stated otherwise.

The term "lower alkoxy" as used herein contemplates both straight and branched chain alkoxy radicals containing from one to four carbon atoms and includes methoxy, ethoxy, isopropoxy and the like.

The basic compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, ether or an ethanol-ether mixture. These salts, when administered to a mammal, possess the same pharmacologic activities as the corresponding bases. For many purposes it is preferable to administer the salts rather than the base compounds. Examples of salts are those with organic acids, e.g. acetic, lactic, succinic, benzoic, salicylic, methanesulfonic or toluenesulfonic acid, as well as polymeric acids such as tannic acid or carboxymethyl cellulose, and salts with inorganic acids such as hydrohalic acids, e.g. hydrochloric acid, phosphoric acid or sulfuric acid. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I which result from asymmetric centers, contained therein.

Antihypertensive Activity

The antihypertensive effect of the compounds of formula I and their acid addition salts is demonstrated in standard pharmacological tests. For example, in tests conducted in the spontaneously hypertensive rat (SHR), such as described by R. Tabei, et al., Clin. Pharmacol. Therap. 11, 269(1970) or I. Varva, et al., Can. J. Physiol. Pharmacol., 51, 727(1973). More specifically exemplified, a testing method such as described in the latter publication show that the preferred compounds 5,6-dihydro-3,3,6-trimethyl-4,1-benzoxazonin-2,7(1H,3H)-dione(Example 3), 1,2,3,5,6,7-hexahydro-3-methyl-2,7-dioxo-4,1-benzoxazonin-3-acetic acid ethyl ester (Example 5), 3-chloromethyl-b 5,6-dihydro-3-methyl-4,1-bezoxazonin-2,7(1H,3H)-dione (Example 6), 1,5,6,7-tetrahydro-7-hydroxy-3,3-dimethyl-7-phenyl-4,1-benzoxazonin-2(3H)-one (Example 16) and 7-amino-1,5,6,7-tetrahydro-3,3-dimethyl-4,1-benzoxazonin-2(3H)-one (Example 20) cause a notable blood pressure decrease in the SHR at about four hours after a dose of 50 – 150mg per kilogram body weight perorally.

When the compounds of formula I or this invention are used as antihypertensive agents in mammals e.g. rats, dogs and mice, they are used alone or in combination with pharmacologically acceptable carriers, the proportion of which is determined by the solubility and chemical nature of the compound, chosen route of administration and standard biological practice. For example, they are administered orally in solid form, i.e. capsule or tablet. They may also be administered orally in the form of suspensions or solutions or they may be injected parenterally. For parenteral administration they may be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets may be uncoated or they may be coated by known techniques so as to delay disintegration and absorption in the gastrointestinal tract and thereby provide a sustained action over a longer period.

The aqueous suspensions of the invention contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions may also contain one or more preservatives, one or more coloring agents, one or more flavouring agents and one or more sweetening agents.

Non-aqueous suspensions may be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions may also contain a sweetening agent, flavouring agent and antioxidant.

The dosage of the 4,1-benzoxazonine derivatives of this invention will vary with the form of administration and the particular compound chosen. Furthermore, it will vary with the particular host as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective antihypertensive amount of the compounds usually ranges from about 1.0 mg to about 500 mg per kilogram body weight per day, although as aforementioned variations will occur. However a dosage level that is in the range of from about 10 mg to about 300 mg per kilogram body weight per day is employed most desirably in order to achieve effective results.

Antibacterial and Antifungal Activity

The 4,1-benzoxazonine derivatives of this invention also exhibit utility as antibacterial agents against a number of gram-positive and gram-negative microorganisms, such as, Staphylococcus pyogenes, both penicillin sensitive and pencillin resistant, Streptococcus faecalis, Escherichia coli, Aerobacter aerogenes, Salmonella pullorum, Pseudomonas aerugenosa, Proteus mirabilis, Proteus vulgaris, Klebsiella pneumoniae and Serratia marcescens, and as antifungal agents against a number of pathogenic fungi, such as Candida albicans, Microsporum gypseum and Trichophyton granulosum, in standard tests for antibacterial and antifungal activity, such as those described in "Antiseptics, Disinfectants, Fungicides and Sterilization", G. F. Reddisch, Ed., 2nd ed., Lea and Febiger, Philadelphia, 1957 or by D. C. Grove and W. A. Randall in "Assay Methods of Antibiotics", Med. Encycl. Inc., New York 1955.

For example, by employing a test like the serial broth dilution, see Grove and Randall, cited above, in which dilutions of the compounds of this invention in nutrient broth are inoculated with the microorganisms or fungi, described above, incubated at 37° C for 2 days, respectively, and examined for the presence of growth, it may be shown that the preferred compounds 5,6-dihydro-3,3,6-trimethyl-4,1-benzoxazonin-2,7(1H,3H)-dione (Example 3), 1,2,3,5,6,7-hexahydro-3-methyl-2,7-dioxo-4,1-benzoxazonin-3-acetic acid ethyl ester (Example 5), 3-chloromethyl-5,6-dihydro-3-methyl-4,1-benzoxazonin-2,7(1H,3H)-dione (Example 6), 1,5,6,7-tetrahydro-7-hydroxy-3,3-dimethyl-7-phenyl-4,1-benzoxazonin-2(3H)-one (Example 16) and 7-amino-1,5,6,7-tetrahydro-3,3-dimethyl-4,1-benzoxazonin-2(3H)-one (Example 20) are able to inhibit growth totally in this system of Proteus vulgaris, Klebsiella pneumoniae and Serratia marcescens at a concentration of 100 mcg/ml or less.

When the compounds of the invention are employed as antibiotic or antifungal agents in mammals, e.g. rats, they may be administered alone or in combination with pharmacologically acceptable carriers. The proportion of the compound is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents as antibiotic or antifungal agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compound of this invention are most desirably administered at a concentration level that will generally afford antibacterially or antifungally effective results without causing any harmful or deleterious side effects and preferably at a level that is in a range of from about 1.0 mg to about 1,000 mg per kilogram body weight per day, although as aforementioned variations will occur. However, a dosage level that is in the range of from about 10 mg to about 500 mg per kilogram body weight per day is most desirably employed in order to achieve effective results.

In addition, the agent may be employed topically. For topical application they may be formulated in the form of solutions, creams, or lotions in pharmaceutically acceptable vehicles containing 0.1–5 percent, preferably 2 percent, of the agent and may be administered topically to the infected area of the skin.

Also the antibacterial properties of the compounds of this invention may be utilized for washing equipment in hospitals, homes and farms, instruments used in medicine and bacteriology, clothing used in bacteriological laboratories, and floors, walls and ceiling in rooms in which a background free of gram-positive and gram-negative microorganisms, such as those listed above, is desired. When employed in this manner the compounds of this invention may be formulated in a number of compositions comprising the active compound and an inert material. In such compositions, while the compounds of formula I of this invention may be employed in concentrations as low as 500 p.p.m., from a practical point of view, it is desirable to use from about 0.10 percent by weight, to about 5 percent by weight or more.

The formulations that may be used for antiseptic wash solutions of the compounds of this invention are varied and may readily be prepared by standard techniques, see for example, "Remington's Practice of Pharmacy," E. W. Martin et al., Eds., 12th ed., Mack Publishing Company, Easton, Pa., 1961, pp. 1,121–1,150. In general, the compounds may be made up in stock solutions. They can also be formulated as suspensions in an aqueous vehicle. These make useful mixtures for decontaminating premises. Also, aqueous vehicles containing emulsifying agents, such as sodium lauryl sulfate, and relatively high concentrations, e.g., up to about 5 percent by weight, of the compounds may be formulated by conventional techniques.

A typical antiseptic preparation useful for disinfecting floors, walls, ceiling, and articles in a contaminated room may be prepared by adding 5 to 25 g of a compound of this invention to a mixture of 150 to 300 g of polyethylene glycol 1,540 and 150 to 300 g of polyethylene glycol 300. The resulting mixture is stirred while a solution of 1 to 10 g of sodium lauryl sulfate in 300 to 400 ml of water is added portionwise. The article to be disinfected is coated or immersed in the preparation for a prolonged time, for example, one hour, and then rinsed with sterile water.

Process

For the preparation of the 4,1-benzoxazonine derivatives of this invention the starting materials, the pyranoindoles of formula II

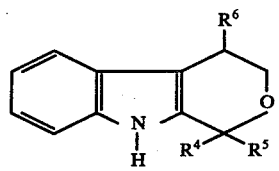

in which $R^4$, $R^5$ and $R^6$ are as defined herein, are either known, for example, see U.S. Pat. No. 3,880,853,
issued Apr. 29, 1975, U.S. Pat. No. 3,843,681, issued October 22, 1974. and C. A. Demerson et al., J. Med. Chem., 18, 189(1975), or they are obtained by the following process:

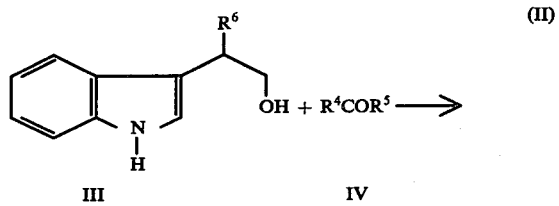

in which $R^4$, $R^5$ and $R^6$ are as defined herein.

With reference to the above scheme an appropriately substituted tryptophol of formula III is condensed with a keto compound of formula IV in the presence of a suitable acid catalyst, for example, the type of catalyst used in a Friedel-Crafts reaction, preferably p-toluenesulfonic acid, boron trifluoride etherate or phosphorus pentoxide, to yield the corresponding starting material of formula II.

For the preparation of the 4,1-benzoxazonine derivative of this invention of formula I in which $R^1$ is hydrogen, $R^2$ and $R^3$ together are oxo, $R^7$ and $R^8$ together are oxo and $R^4$, $R^5$ and $R^6$ are as defined herein, the following process shown schematically below is both practical and convenient:

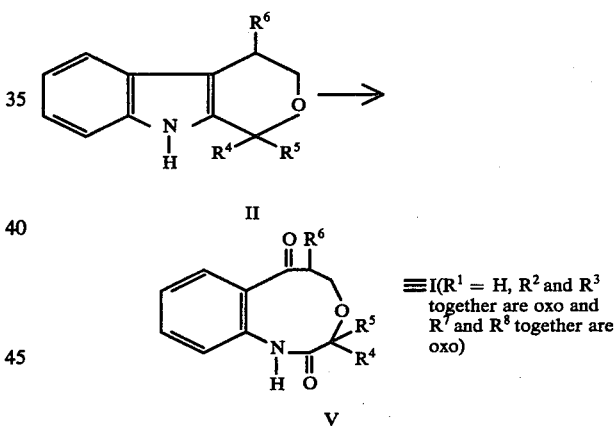

in which $R^4$, $R^5$ and $R^6$ are as defined herein. (For convenience and clarity these compounds of formula I are represented above as formula V).

With reference to the above scheme the starting material of formula II is oxidized, whereupon the indole double bond is oxidatively cleaved, to yield the corresponding compound of formula V.

The oxidative cleavage of indolic double bonds is well documented. Suitable reagents are ozone, organic peracids, hydrogen peracids, oxygen and sodium periodate. Examples of typical methods include ozonolysis, described by B. Witkop and J. Patrick, J. Amer. Chem. Soc., 74, 3855(1972) and B Witkop and S. Goodwin, J. Amer. Chem. Soc., 74, 337(1953), oxidation by peracids, described by B. Witkop, J. Amer. Chem. Soc., 72, 1428(1950), autoxidation, described by B. Witkop and J. Patrick, J. Amer. Chem. Soc., 73, 2196(1951) and E. Winterfeldt, Liebigs Ann. Chem., 745, 23(1971) and sodium periodate oxidation, described by L. J. Dolby and D. L. Booth, cited above. The latter method using sodium periodate oxidation is the method of choice for the oxidation of the starting material of formula II since it is facile and gives good yields.

In practising the oxidation (II → V) it is preferable to add a solution of the starting material of formula II in a solvent inert to the reactants, for example, tetrahydrofuran, dioxane or a lower alkanol, preferably methanol, ethanol or propanol, to a solution containing about two to ten molar equivalents, preferably two to three molar equivalents of sodium periodate in water. The time of the reaction may range from one hour to 60 hours, with the preferred range from five to 30 hours. The temperature of the reaction may range from 0° C to the boiling point of the reaction mixture, with the preferred temperature range being from 10° to 50° C. The compounds of formula V are isolated from the reaction mixture by conventional methods, for example, filtration, evaporation, extraction, chromatography and/or crystallization.

The compounds of formula V are readily transformed to the corresponding compounds of formula I by methods disclosed below.

The compound of formula I in which $R^4$, $R^5$ and $R^6$ are as defined herein, $R^1$ and $R^8$ are hydrogen, $R^2$ and $R^3$ together are oxo and $R^7$ is hydroxy is readily obtained by reducing the corresponding compound of formula V in which $R^4$, $R^5$ and $R^6$ are as defined herein. Suitable reducing agents are selected from hydrogen in the presence of a noble metal catalyst, for example, platinum or palladium on carbon, a suitable complex borohydride, for example, sodium borohydride or lithium borohydride or a suitable complex metal hydride, for instance lithium aluminum hydride. Sodium borohydride is the preferred reducing agent. When sodium borohydride is used preferred solvents for the reaction include methanol, tetrahydrofuran and the like. When lithium aluminum hydride is used as the reducing agent, preferred solvents include the non-hydroxylic solvents, for example, diethyl ether, dioxane, tetrahydrofuran, 1,2-dimethoxyethane and the like. Generally the reaction is best performed at temperatures ranging from 0° to 40° C, preferably from 20° to 30° C, for periods varying from 30 minutes to 24 hours. While equivalent quantities of reactants may be used, it is preferable to use the reducing agent in moderate excess. The latter compounds of formula I are isolated from the reaction mixture by conventional methods, for instance, see the Examples.

The compound of formula I in which $R^4$ and $R^6$ are as defined herein, $R^1$, $R^2$, $R^3$ and $R^8$ are hydrogen, $R^5$ is lower alkyl and $R^7$ is hydroxy is obtained by reducing the corresponding compound of formula V in which $R^4$ and $R^6$ are as defined herein and $R^5$ is lower alkyl with a suitable complex metal hydride. In this case lithium aluminum hydride is the preferred reducing agent. Preferred solvents include the non-hydroxylic solvents mentioned for the above reduction and the preferred temperature range of the reaction is 60° to 100° C or at the boiling point of the reaction mixture. The time of the reaction may vary from two to 30 hours.

The latter compound of formula I can be further N-acylated at the 1 position to obtain a corresponding haloalkanoylate intermediate. A convenient and practical method for this acylation is under Schotten-Baumann conditions using a halo(lower)alkanoyl halide of formula (Halogen)—CO(CH$_2$)$_n$—(Halogen) in which the halogens are selected from bromine, iodine or chlorine. A preferred method for effecting this N-acylation comprises bringing the reactants together in the presence of a molar excess, preferably 1.1 to 3 molar equivalents, of a base. Suitable bases for this purpose are the alkali metal carbonates and hydroxides, for instance, potassium or sodium carbonate or potassium or sodium hydroxide. Suitable solvents include those which are inert to the reaction conditions, a preferred solvent is a mixture of water and an aromatic hydrocarbon, for example, benzene or toluene. The temperature and duration of the reaction are not critical; however, it is most convenient and efficacious to carry out the reaction at a temperature from about 0° C to about 30° C for a period about 30 minutes to about 10 hours.

The requisite halo(lower)alkanoyl halides are either known or are prepared by known methods; for example, see "Rodd's Chemistry of Carbon Compounds", S. Coffey, Ed. Vol. 1c, 2nd ed., Elsevier Publishing Co., Amsterdam, 1965, pp 201–215.

The N-acylated intermediate is subjected to amination conditions to obtain the corresponding compound of formula I in which $R^4$ and $R^6$ are as defined herein, $R^1$ is CO(CH$_2$)$_n$NR$^9$, $R^{10}$ wherein n, $R^9$ and $R^{10}$ are as defined herein, $R^2$, $R^3$ and $R^8$ are hydrogen, $R^5$ is lower alkyl and $R^7$ is hydroxy. A convenient method for preparing the latter described amine of formula I comprises reacting said haloalkanoylate intermediate with a molar excess, preferably 5 to 15 molar equivalents of an amine of formula HNR$^9$R$^{10}$ in which $R^9$ and $R^{10}$ are as defined herein. The amination is preferably performed in a suitable inert solvent, for example, tetrahydrofuran, water, methanol, dioxane, and the like or a mixture thereof, at 0° to 100° C for a period of 30 minutes to 20 hours.

Thereafter the latter compound of formula I can be reacted with a suitable complex metal hydride in the manner as described above to obtain the corresponding compound of formula I in which $R^4$ and $R^6$ are as defined herein, $R^1$ is CH$_2$(CH$_2$)$_n$NR$^9$R$^{10}$ wherein n, $R^9$ and $R^{10}$ are as defined herein, $R^2$, $R^3$ and $R^8$ are hydrogen, $R^5$ is lower alkyl and $R^7$ is hydroxy. In this case the preferred complex metal hydride is lithium aluminum hydride and the preferred solvents include those mentioned above for use with lithium aluminum hydride. The preferred temperature of the reaction is 60° to 100° C or at the boiling point of the reaction mixture and the time of the reaction may vary from two to 30 hours.

The compound of formula I in which $R^4$, $R^5$ and $R^6$ are as defined herein, $R^1$ is hydrogen, $R^2$ and $R^3$ together are oxo, $R^7$ is hydroxy and $R^8$ is lower alkyl or phenyl is obtained by reacting the corresponding compound of formula V in which $R^4$, $R^5$ and $R^6$ are as defined herein, with a Grignard reagent. Suitable Grignard reagents are selected from lower alkyl and phenyl magnesium halides wherein the halide is selected from chlorine, bromine or iodine. Convenient and practical conditions for this Grignard reaction comprises; ether or tetrahydrofuran as the solvent for the reaction, a reaction time of from five minutes to six hours and a reaction temperature of from −25° C to the boiling point of the reaction mixture, preferably from 30° C to the boiling point of the reaction mixture.

The latter compound of formula I in which $R^4$ and $R^6$ are as defined herein, $R^1$ is hydrogen, $R^2$ and $R^3$ together are oxo, $R^5$ is lower alkyl, $R^7$ is hydroxy and $R^8$ is lower alkyl or phenyl can be reacted with a suitable complex metal hydride in the manner as described above to give the corresponding compound of formula I in which $R^4$ and $R^6$ are as defined herein, $R^1$, $R^2$ and $R^3$ are hydrogen, $R^5$ is lower alkyl, $R^7$ is hydroxy and $R^8$ is lower alkyl or phenyl. For this reduction, lithium aluminum hydride is the preferred complex metal hydride. Preferred solvents include those mentioned above for use with lithium aluminum hydride and the preferred temperature range of the reaction is 60° to 100° C or at the boiling point of the reaction mixture. The time of the reaction may vary from two to 30 hours.

The latter compound of formula I can be reacted with a Halogen(lower)alkanoyl halide of formula (Halogen)-$CO(CH_2)_n$(Halogen) followed by treatment with an amine of formula $HNR^9R^{10}$ in which $R^9$ and $R^{10}$ are as defined herein, in the same manner as described above, to give the corresponding compound of formula I in which $R^4$ and $R^6$ are as defined herein, $R^1$ is $CO(CH_2)_nNR^9R^{10}$ wherein n, $R^9$ and $R^{10}$ are as defined herein, $R^2$ and $R^3$ are hydrogen, $R^5$ is lower alkyl, $R^7$ is hydroxy and $R^8$ is lower alkyl or phenyl.

If desired, reduction of the latter compound of formula I, preferably with lithium aluminum hydride in the same manner as described above, gives the corresponding compound of formula I in which $R^4$ and $R^6$ are as defined herein, $R^1$ is $CH_2(CH_2)_nNR^9R^{10}$ wherein n, $R^9$ and $R^{10}$ are as defined herein, $R^2$ and $R^3$ are hydrogen, $R^5$ is lower alkyl, $R^7$ is hydroxy and $R^8$ is lower alkyl or phenyl.

Another transformation of the compound of formula V gives the compound of formula I in which $R^4$, $R^5$ and $R^6$ are as defined herein, $R^1$ and $R^7$ is hydrogen, $R^2$ and $R^3$ together are oxo and $R^8$ is amino. This transformation is effected by converting the corresponding compound of formula V in which $R^4$, $R^5$ and $R^6$ are as defined herein to the corresponding oxime, followed by reducing the oxime. A preferred process for the preparation of the latter compound of formula I comprises reacting the corresponding compound of formula V with a molar excess, preferably two to five molar equivalents, of hydroxylamine in the presence of two to five molar equivalents of a mild base, preferably sodium acetate, sodium bicarbonate or triethylamine, in an inert solvent, preferably a lower alkanol, for example, ethanol or methanol, to obtain the corresponding oxime. The temperature and duration of the reaction are not critical; however, the preferred conditions are a temperature of about 0° to 50° C for about 10 hours to 3 days. The oxime so obtained is reduced to give the corresponding compound of formula I in which $R^4$, $R^5$ and $R^6$ are as defined herein, $R^1$ and $R^7$ are hydrogen, $R^2$ and $R^3$ together are oxo and $R^8$ is amino. A preferred method of reduction comprises hydrogenating the oxime in the presence of a catalytic amount of a noble metal catalyst, for example, palladium or platinum on carbon, in a suitable solvent, for instance, a lower alkanol, preferably methanol or ethanol.

The following examples illustrate further this invention.

EXAMPLE 1

5,6-Dihydro-3,3-dimethyl-4,1-benzoxazonin-2,7(1H,3H)-dione (V; $R^4$ and $R^5$ = $CH_3$ and $R^6$ = H)

A solution of the compound of formula II, 1,3,4,9-tetrahydro-1,1-dimethylpyrano[3,4-b]indole (25.7 g, 0.127 M), in 587 ml of ethanol is added dropwise to a solution of sodium metaperiodate (60.6 g) in 311 ml of water. The solution is stirred at room temperature for 24 hours. The resulting precipitate is collected by filtration, washed with methanol and discarded. The filtrate is concentrated under reduced pressure, water is added and the precipitate is collected. The filtrate is extracted with dichloromethane. The organic extract is washed with water, dried and evaporated. The residue is combined with the latter precipitate, dissolved in acetone, treated with charcoal, filtered and concentrated to obtain crystals of the title compound, mp 146°–148° C.

In the same manner but replacing sodium metaperiodate with other oxidants, for instance ozone, peracids, for example perbenzoic acid or peracetic acid, or molecular oxygen in the presence of a platinum catalyst, the title compound is obtained.

The procedure of Example 1 is followed to prepare other compounds of formula V in which $R^4$, $R^5$ and $R^6$ are as defined in the first instance. Examples of such compounds are listed in Table 1. In each of these examples an equivalent amount of the appropriate starting material of formula II listed therein is used instead of the starting material of formula II described in the procedure of Example 1.

TABLE I

| | Starting Material of Formula II | | | Product: [(prefix listed below)-4,1-benzoxazonin-(suffix listed below)] |
|---|---|---|---|---|
| Ex. | $R^4$ | $R^5$ | $R^6$ | Prefix/Suffix |
| 2 | $CH_3$ | $CH_3$ | H | 5,6-dihydro-3,3-dimethyl//2,7(1H,3H)-dione |
| 3 | $CH_3$ | $CH_3$ | $CH_3$ | 5,6-dihydro-3,3,6-trimethyl//2,7(1H,3H)-dione; mp 177–178° C |
| 4 | $CH_3$ | 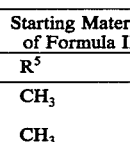 $CH_2CN(CH_3)_2$ | H | 1,2,3,5,6,7-hexahydro-N,N,3-trimethyl-2,7-dioxo//3-acetamide; mp 164–165° C |
| 5 | $CH_3$ | 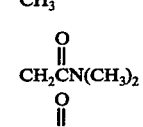 $CH_2COC_2H_5$ | H | 1,2,3,5,6,7-hexahydro-3-methyl-2,7-dioxoll 3-acetic acid ethyl ester; mp 155–158° C |
| 6 | $CH_3$ | $CH_2Cl$ | H | 3-chloromethyl-5,6-dihydro-3-methyl//2,7-(1H,3H)-dione; mp 172–173° C |
| 7 | $C_3H_7$ | $C_3H_7$ | $C_4H_9$ | 6-butyl-3,3-dipropyl-5,6-dihydro//2,7-(1H,3H)dione |
| 8 | $C_2H_5$ | $C_4H_9$ | $C_5H_{11}$ | 3-butyl-3-ethyl-6-pentyl-5,6-dihydro//2,7(1H,3H)dione |
| 9 | $CH_3$ | 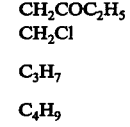 $C_3H_6CN(C_2H_5)_2$ | $C_2H_5$ | 1,2,3,5,6,7-hexahydro-3-methyl-N,N,6-triethyl-2,7-dioxo//3-butanamide |
| 10 | $C_6H_{13}$ | 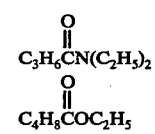 $C_4H_8COC_2H_5$ | H | 1,2,3,5,6,7-hexahydro-3-hexyl-2,7-dioxo//3-pentanoic acid ethyl ester |
| 11 | $CH_2CH(CH_3)_2$ | $C_2H_4I$ | $CH(CH_3)_2$ | 5,6-dihydro-3-(2-iodoethyl)-6-(1-methylethyl)-3-(2-methylpropyl)//2,7(1H,3H)-dione |

TABLE I-continued

| Ex. | Starting Material of Formula II | | | Product: [(prefix listed below)-4,1-benzoxazonin-(suffix listed below)] |
|---|---|---|---|---|
| | $R^4$ | $R^5$ | $R^6$ | Prefix/Suffix |
| 12 | $C_2H_5$ | $\underset{C_2H_4CN(CH_3)_2}{O\atop\|}$ | $C_6H_{13}$ | 1,2,3,5,6,7-hexahydro-3-ethyl-6-hexyl-N,N-dimethyl-2,7-dioxo//3-propanamide |
| 13 | $CH_3$ | $\underset{C_2H_4COC_3H_7}{O\atop\|}$ | $CH_3$ | 1,2,3,5,6,7-hexahydro-3,6-dimethyl-2,7-dioxo//3-propanoic acid propyl ester |

EXAMPLE 14

1,5,6,7-Tetrahydro-7-hydroxy-3,3-dimethyl-4,1-benzoxazonin-2(3H)-one (1; $R^1$, $R^6$, and $R^8$ = H, $R^2$ and $R^3$ together are oxo, $R^4$ and $R^5$ = $CH_3$ and $R^7$ is OH)

The compound of formula V, 5,6-dihydro-3,3-dimethyl-4,1-benzoxazonin-2,7-(1H,3H)-dione (described in Example 1, 20 g), is added portionwise to a cooled mixture of sodium borohydride (20 g), in 500 ml of methanol. The mixture is stirred at room temperature for 2 hours and evaporated. Water is added to the residue and the aqueous solution is extracted with chloroform. The organic extract is washed with water, dried and evaporated. The residue is crystallized from acetonitrile to give the title compound, mp 141°–142° C.

In the same manner but replacing sodium borohydride in methanol with an equivalent amount of lithium aluminum hydride in tetrahydrofuran, the title compound is obtained.

In the same manner but replacing the starting material of formula V with other starting materials of formula V described in Examples 2, 4, and 5, 1,5,6,7-tetrahydro-1-chloro-7-hydroxy-3,3-dimethyl-4,1-benzoxazonin-2(3H)-one, 1,2,3,5,6,7-hexahydro-7-hydroxy-N,N,3-trimethyl-2-oxo-4,1-benzoxazonin-3-acetamide and 1,2,3,5,6,7-hexahydro-7-hydroxy-3-methyl-2-oxo-4,1-benzoxazonin-3-acetic acid ethyl ester are obtained, respectively.

EXAMPLE 15

1,2,3,5,6,7-Hexahydro-3,3-dimethyl-4,1-benzoxazonin-7-ol (1; $R^1$, $R^2$, $R^3$, $R^6$ and $R^8$ = H, $R^4$ and $R^5$ = $CH_3$ and $R^7$ = OH)

A solution of the compound of formula V, 5,6-dihydro-3,3-dimethyl-4,1-benzoxazonin-2,7(1H,3H)-dione (described in Example 1, 15g), in tetrahydrofuran (300 ml) is added dropwise to an ice-bath cooled mechanically stirring mixture of lithium aluminum hydride (12.16 g) in tetrahydrofuran (250 ml). After completion of the addition the mixture is heated at reflux for 24 hr. and cooled in an ice-bath. A solution of water (12 ml) and tetrahydrofuran (20 ml) is slowly added, followed by the addition of 12 ml of 20% sodium hydroxide solution and again followed by water (42 ml). The mixture is filtered and the filtrate is concentrated. Water is added to the residue and the mixture is extracted with chloroform. The organic extract is washed with water, dried and evaporated. The residue is crystallized from acetone to give the title compound, mp 148.5°–151.5° C. The title compound is dissolved in dry methanol and an equivalent amount of anhydrous hydrogen chloride in dry diethyl ether is added. The crystals are collected to obtain the title compound as the hydrochloride salt, mp 178°–180° C.

In the same manner but replacing the starting material of formula V with other starting materials of formula V described in Examples 3, 7 and 8, 1,2,3,5,6,7-hexahydro-3,3,6-trimethyl-4,1-benzoxazonin-7-ol, 1,2,3,5,6,7-hexahydro-6-butyl-3,3-dipropyl-4,1-benzoxazonin-7-ol and 1,2,3,5,6,7-hexahydro-3-butyl-3-ethyl-6-pentyl-4,1-benzoxazonin-7-ol are obtained, respectively.

EXAMPLE 16

1,5,6,7-Tetrahydro-7-hydroxy-3,3-dimethyl-7-phenyl-4,1-benzoxazonin-2(3H)-one (1; $R^1$ and $R^6$ = H, $R^2$ and $R^3$ together are oxo, $R^4$ and $R^5$ = $CH_3$ $R^7$ = OH and $R^8$ = phenyl)

Bromobenzene in dry diethyl ether (30 ml) is added to magnesium turnings (4.8 g) in dry diethyl ether (50 ml) and the mixture is heated at reflux for ten minutes. A solution of the compound of formula V, 5,6-dihydro-3,3-dimethyl-4,1-benzoxazonin-2,7(1H,3H)-dione (described in Example 1, 11.7 g), in tetrahydrofuran (100 ml) is added and the solution is heated at reflux for 2 hours. Saturated aqueous ammonium chloride solution is added and the mixture is extracted with chloroform. The organic extract is dried and evaporated. The residue is crystallized from benzene-acetonitrile to give the title compound, mp 131°–131.5° C.

In the same manner but replacing the above Grignard reagent with appropriate Grignard reagents and replacing the starting material of formula V with those described in Examples 3,8, 10 and 12, 1,5,6,7-tetrahydro-7-hydroxy-7-butyl-3,3,6-trimethyl-4,1-benzoxazonin-2(3H)-one, 1,5,6,7-tetrahydro-7-hydroxy-3-butyl-3-ethyl-7-methyl-6-pentyl-4,1-benzoxazonin-2(3H)-one, 1,2,3,5,6,7-hexahydro-7-hydroxy-3-hexyl-7-phenyl-2-oxo-4,1-benzoxazonin-3-pentanoic acid ethyl ester and 1,2,3,5,6,7-hexahydro-7-hydroxy-3-ethyl-6-hexyl-7-propyl-N,N-dimethyl-2oxo-4,1-benzoxazonin-3-propanamide are obtained, respectively.

EXAMPLE 17

1,2,3,5,6,7-Hexahydro-3,3-dimethyl-7-phenyl-4,1-benzoxazonin-7ol (1; $R^1$, $R^2$, $R^3$ and $R^6$ = H, $R^4$ and $R^5$ = $CH_3$, $R^7$ = OH and $R^8$ = phenyl)

A solution of 1,5,6,7-tetrahydro-7-hydroxy-3,3-dimethyl-7-phenyl-4,1-benzoxazonin-2(3H)-one (described in Example 16, 8.0 g) in tetrahydrofuran (100 ml) is added to a mixture of lithium aluminum hydride (8.0 g) in tetrahydrofuran (100 ml). The mixture is heated at reflux for 24 hours. Water (28 ml) followed by 20% sodium hydroxide (6 ml) is added. The mixture is filtered and the filtrate is evaporated to remove the tetrahydrofuran. Water is added and the aqueous solution is extracted with chloroform. The organic extract is dried and evaporated. The residue is crystallized from ethanol to give the title compound, mp 147°–148° C. The title compound is dissolved in dry ethanol and an equivalent amount of anhydrous hydrogen chloride in dry ether is added. The crystals are collected to obtain the title compound as the hydrochloride salt, mp 210° C (dec.).

In the same manner but replacing the starting material with 1,5,6,7-tetrahydro-7-hydroxy-7-butyl-3,3,6-trimethyl-4,1-benzoxazonin-2(3H)-one or 1,5,6,7tetrahydro-7-hydroxy-3butyl-3ethyl-7-methyl-6pentyl-4,1-benzoxazonin-2(3H)-one described in Example 16, 1,2,3,5,6,7-hexahydro-7-butyl-3,3,6-trimethyl-4,1-benzoxazonin-7-ol and 1,2,3,5,6,7-hexahydro-3-butyl-3-ethyl-7-methyl-6-pentyl-4,1-benzoxazonin-7-ol are obtained, respectively.

EXAMPLE 18

1-(N,N-Dimethylaminoacetyl)-1,2,3,5,6,7-hexahydro-3,3-dimethyl-4,1-benzoxazonin-7-ol (1; $R^1 =$ $COCH_2N(CH_3)_2$, $R^2$, $R^3$, $R^6$ and $R^8 =$ H, $R^4$ and $R^5 =$ $CH_3$, and $R^7 =$ OH Bromoacetyl bromide (14.0 g) is slowly added to a stirring solution at 0° C of 1,2,3,5,6,7-hexahydro-3,3-dimethyl-4,1-benzoxazonin-7-ol (described in Example 15, 14.0 g) in benzene (400 ml) and 2N sodium hydroxide (45 ml). After stirring for one hour, additional 2N sodium hydroxide (20 ml) is added and stirring is continued for 40 min. The two phases are separated and the aqueous phase is extracted with benzene. The combined organic phases are washed with 2N hydrochloric acid, water, dried and evaporated. The residue is crystallized from benzene-petroleum ether to give 1-bromoacetyl-1,2,3,5,6,7-hexahydro-3,3-dimethyl-4,1-benzoxazonin-7-ol, nmr(CDCl$_3$) δ 1.09(S, 3H), 1.35(S, 3H), 3.09 and 4.38 (doublets, J = 15 Hz, 2H), 5.04(d, J = 4 Hz, 1H) and 6.9–7.8 ppm (m, 4H).

A mixture of the latter compound (12.65 g), 40% aqueous dimethylamine (175 ml) and tetrahydrofuran (250 ml) is stirred at room temperature for 2 hours. After the tetrahydrofuran is removed by evaporation, the residue is diluted with water and extracted with chloroform. The organic extract is dried and evaporated. The residue is crystallized from ethyl acetate-petroleum ether to give the title compound, mp 113°–115° C. The title compound is dissolved in dry methanol and an equivalent amount of anhydrous hydrogen chloride in dry ether is added. The crystals are collected to obtain the title compound as the hydrochloride salt, mp 266°–268° C.

In the same manner but replacing bromoacetyl bromide with 4-chloro-butanoyl chloride and replacing dimethylamine with propylamine as well as replacing the starting material of formula I with the corresponding starting materials of formula I described in Examples 15 and 17, the following compounds of formula I are obtained: 1-[4-(propylamino)-1-oxobutyl]-1,2,3,5,6,7-hexahydro-3,-3,6-trimethyl-4,1-benzoxazonin-7-ol, 1-[4-(propylamino)-1-oxobutyl]-1,2,3,5,6,7-hexahydro-6-butyl-3,3-dipropyl-4,1-benzoxazonin-7-ol, 1-[4-(propylamino)-1-oxobutyl]-1,2,3,5,6,7-hexahydro-3-butyl-3-ethyl-6-pentyl-4,1-benzoxazonin-7-ol, 1,2,3,5,6,7-hexahydro-1-[4-propylamino)-1-oxobutyl]-3,3-dimethyl-7-phenyl-4,1-benzoxazonin-7-ol, 1,2,3,5,6,7-hexahydro-1-(propylamino)-1-oxobutyl]-7-butyl-3,3,6-trimethyl-4,1-benzoxazonin-7-ol and 1,2,3,5,6,7-hexahydro-1-[4-(propylamino)-1-oxobutyl]-3-butyl-3-ethyl-7-methyl-6-pentyl-4,1-benzoxazonin-7-ol.

EXAMPLE 19

1-[2-(Dimethylamino)ethyl]-1,2,3,5,6,7-hexahydro-3,3-dimethyl-4,1-benzoxazonin-7-ol (1; $R^1 =$ $(CH_2)_2N(CH_3)_2$, $R^2$, $R^3$, $R^6$ and $R^8 =$ H $R^4$ and $R^5 =$ $CH_3$ and $R^7 =$ OH A mixture of 1-(N,N-dimethylaminoacetyl)-1,2,3,5,6,7-hexahydro-3,3-dimethyl-4,1-benzoxazonin-7-ol (described in Example 18, 5.2 g) and lithium aluminum hydride (5.0 g) in tetrahydrofuran (150 ml) is heated at reflux with stirring for 18 hr. The excess lithium aluminum hydride is decomposed with water. The mixture is filtered and the filtrate is evaporated. The residue is diluted with water and extracted with chloroform. The organic extract is dried and evaporated to give the title compound, nmr (DMSO-d$_6$) δ 0.88 (s, 3H), 1.23 (s, 3H), 2.42 (s, 6H), 5.6 (m, 1H) and 7.1–7.5 ppm (m, 4H). The title compound is dissolved in dry methanol and an equivalent amount of anhydrous hydrogen chloride in dry ether is added. The crystals are collected to obtain the hydrochloride salt of the compound, mp 253°–254° C.

In the same manner but replacing the starting material of formula I with the other starting materials of formula I described in Example 18, 1-[4-(propylamino)-butyl]-1,2,3,5,6,7-hexahydro-3,3,6-trimethyl-4,1-benzoxazonin-7-ol, 1-[4-(propylamino)butyl]-1,2,3,5,6,7-hexahydro-6-butyl-3,3-dipropyl-4,1-benzoxazonin-7-ol, 1-[3-(propylamino)-butyl-1,2,3,5,6,7-hexahydro-3-butyl-3-ethyl-6-pentyl-4,1-benzoxazonin-7-ol, 1,2,3,5,6,7-hexahydro-1-[4-(propylamino)butyl]-3,3-dimethyl-7-phenyl-4,1-benzoxazonin-7-ol, 1,2,3,5,6,7-hexahydro-1-[4-(propylamino)-butyl]-7-butyl-3,3,6-trimethyl-3,3,6-trimethyl-4,1-benzoxazonin-7-ol and 1,2,3,5,6,7-hexahydro-1-[4-(propylamino)butyl]-3-butyl-3-ethyl-6-pentyl-4,1-benzoxazonin-7-ol are obtained.

EXAMPLE 20

7-Amino-1,5,6,7-tetrahydro-3,3-dimethyl-4,1-benzoxazonin-2(3H)-one (1; $R^1$, $R^6$ and $R^7 =$ H, $R^2$ and $R^3$ together are oxo, $R^4$ and $R^5 =$ $CH_3$ and $R^8 =$ $NH_2$)

A solution of the compound of formula V, 5,6-dihydro-3,3-dimethyl-4,1-benzoxazonine-2,7(1H,3H)-dione (described in Example 1, 50 g), sodium acetate (37.5 g) and hydroxylamine hydrochloride (31.5 g) in ethanol (1,200 ml) is stirred at room temperature for two days. The precipitate is removed by filtration and the filtrate evaporated. Water and diethyl ether are added to the residue. The organic phase is separated, dried and evaporated. The residue is crystallized from ethanol to give 5,6-dihydro-3,3-dimethyl-4,1-benzoxazonin-2,7(1H,3H)-dione 7-oxime, mp 205°–206° C.

A mixture of the above oxime (1.0 g) and 5% palladium on carbon (0.20 g) in absolute ethanol (100 ml) and hydrochloric acid (0.4 ml) is rapidly stirred under an atmosphere of hydrogen for 18 hours. The catalyst is removed by filtration and the filtrate is evaporated. The residue is crystallized from ethanol to obtain the hydrochloride salt of the title compound, mp 165°–167° C. The corresponding free base has $\gamma_{max}^{CHCl_3}$ 3400 cm$^{-1}$.

In the same manner but replacing the starting material of formula V with other starting materials of formula V, for instance those described in Examples 3, 4, and 12: 7-amino-1,5,6,7-tetrahydro-3,3,6-trimethyl-4,1-benzoxazonin-2(3H)-one, 1,2,3,5,6,7-hexahydro-7-amino-N,N,3-trimethyl-2-oxo-4,1-benzoxazonine-3- acetamide and 1,2,3,5,6,7-hexahydro-amino-3ethyl-6-hexyl-N-N-dimethyl-2-oxo-4,1-benzoxaonine-3-propanamine are obtained, respectively.

We claim:

1. A compound of formula I

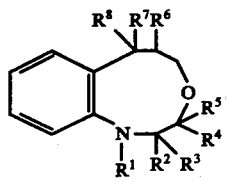

(1)

in which $R^1$ is hydrogen, $CO(CH_2)_nNR^9R^{10}$ wherein n is an integer from 1 to 4 and $R^9$ and $R^{10}$ each is hydrogen or lower alkyl, or $CH_2(CH_2)_nNR^9R^{10}$ wherein n, $R^9$ and $R^{10}$ are as defined herein; $R^2$ is hydrogen; $R^3$ is hydrogen; or $R^2$ and $R^3$ together are oxo; $R^4$ is lower alkyl; $R^5$ is lower alkyl or $(CH_2)_pY$ wherein p is an integer from 1 to 5 and Y is halo, lower alkoxycarbonyl or $CONR^{11}R^{12}$ wherein $R^{11}$ and $R^{12}$ each is hydrogen or lower alkyl; $R^6$ is hydrogen or lower alkyl; and $R^7$ is hydrogen and $R^8$ is amino; or $R^7$ is hydroxy and $R^8$ is hydrogen, lower alkyl or phenyl; or $R^7$ and $R^8$ together are oxo, with the proviso that when $R^2$ and $R^3$ together are oxo and $R^4$, $R^5$, $R^6$, $R^7$ and $R^8$ are as defined herein then $R^1$ is hydrogen; and with the additional proviso that when $R^2$ and $R^3$ are hydrogen and $R^1$, $R^4$ and $R^6$ are as defined herein then $R^5$ is lower alkyl; $R^7$ is hydroxy; and $R^8$ is hydrogen, lower alkyl or phenyl, or a therapeutically acceptable salt thereof.

2. A compound of formula I

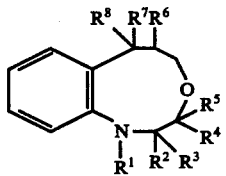

(1)

in which $R^1$ is hydrogen; $R^2$ and $R^3$ are oxo; $R^4$ is lower alkyl; $R^5$ is lower alkyl, $(CH_2)_pY$ wherein p is an integer from 1 to 5 and Y is halo, lower alkoxycarbonyl or $CONR^{11}R^{12}$ wherein $R^{11}$ and $R^{12}$ each is hydrogen or lower alkyl; $R^6$ is hydrogen or lower alkyl; $R^7$ is hydrogen; and $R^8$ is amino; or $R^7$ is hydroxy and $R^8$ is hydrogen, lower alkyl or phenyl; or $R^7$ and $R^8$ together are oxo; or a therapeutically acceptable salt thereof.

3. A compound of formula I

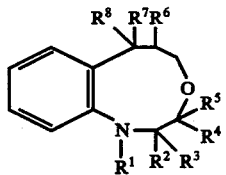

(1)

in which $R^1$ is hydrogen, $CO(CH_2)_nNR^9R^{10}$ wherein n is an integer from 1 to 4,, $R^9$ and $R^{10}$ each is hydrogen or lower alkyl, or $CH_2(CH_2)_nNR^9R^{10}$ wherein n is an integer from 1 to 4, $R^9$ and $R^{10}$ each is hydrogen or lower alkyl; $R^2$ is hydrogen; $R^3$ is hydrogen; $R^4$ is lower alkyl; $R^5$ is lower alkyl; $R^6$ is hydrogen or lower alkyl; $R^7$ is hydroxy; and $R^8$ is hydrogen, lower alkyl or phenyl; or a therapeutically acceptable salt thereof.

4. 5,6-Dihydro-3,3-dimethyl-4,1-benzoxazonine-2,7(1H,3H)-dione, as claimed in claim 1.

5. 5,6-Dihydro-3,3,6-trimethyl-4,1-benzoxazonin-2,7(1H,3H)-dione, as claimed in claim 1.

6. 1,2,3,5,6,7-Hexahydro-N,N,3-trimethyl-2,7-dioxo-4,1-benzoxazonin-3-acetamide, as claimed in claim 1.

7. 1,2,3,5,6,7-Hexahydro-3-methyl-2,7-dioxo-4,1-benzoxazonin-3-acetic acid ethyl ester, as claimed in claim 1.

8. 1,2,3,5,6,7-Hexahydro-3,3-dimethyl-2,7-dioxo-4,1-benzoxazonin-9-carboxylic acid methyl ester, as claimed in claim 1.

9. 3-Chloromethyl-5,6-dihydro-3-methyl-4,1-benzoxazonin-2,7(1H,3H)-dione, as claimed in claim 1.

10. 1,5,6,7-Tetrahydro-7hydroxy-3,3-dimethyl-4,1-benzoxazonin-2(3H)-one, as claimed in claim 1.

11. 1,2,3,5,6,7-Hexahydro-3,3-dimethyl-4,1-benzoxazonin-7-ol, as claimed in claim 1.

12. 1-(N,N-Dimethylaminoacetyl)-1,2,3,5,6,7-hexahydro-3,3-dimethyl-4,1-benzoxazonin-7-ol, as claimed in claim 1.

13. 1-[2-(Dimethylamino)ethyl]-1,2,3,5,6,7-hexahdro-3,3-dimethyl-4,1-benzoxazonin-7-ol, as claimed in claim 1.

14. 1,5,6,7-Tetrahydro-7-hydroxy-3,3-dimethyl-7-phenyl-4,1-benzoxazonin-2(3H)-one, as claimed in claim 1.

15. 1,2,3,5,6,7-Hexahydro-3,3-dimethyl-7-phenyl-4,1-benzoxazonin-7-ol, as claimed in claim 1.

16. 7-Amino-1,5,6,7-tetrahydro-3,3-dimethyl-4,1-benzoxazonin-2(3H)-one, as claimed in claim 1.

17. The process for preparing a compound of formula I in claim 1, comprising: oxidizing a compound of formula II

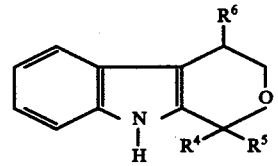

(II)

in which $R^4$, $R^5$ and $R^6$ are as defined therein with an oxidizing amount of a reagent selected from ozone, organic peracids, hydrogen peracids, oxygen or sodium periodate in a solvent inert to the reactants selected from tetrahydrofuran, dioxane, or a lower alkanol containing from one to three carbon atoms at a temperature ranging from 0° C to the boiling point of the reaction mixture for about 1–60 hours to obtain the corresponding compound of formula V:

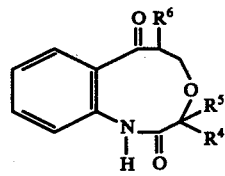

(V)

in which $R^4$, $R^5$ and $R^6$ are as defined therein.

18. The process as claimed in claim 17 which further comprises:

reducing said compound of formula V in which $R^4$, $R^5$ and $R^6$ are as defined therein with a reducing amount of a reagent selected from hydrogen in the presence of a noble metal catalyst, a complex borohydride or a complex metal hydride in an inert organic solvent at a temperature ranging from 0° C to 40° C for about 30 minutes to 24 hours to obtain the corresponding compound of formula I in which $R^4$, $R^5$ and $R^6$ are as defined herein, $R^1$ is hydrogen, $R^2$ and $R^3$ together are oxo, and $R^7$ is hydroxy and $R^8$ is hydrogen.

19. The process as claimed in claim 17 which further comprises:
reacting said compound of formula V in which $R^4$, $R^5$ and $R^6$ are as defined therein with a molar excess of hydroxylamine in the presence of a mild base in an inert organic solvent at a temperature of about 0° C to 50° C for about 10 hours to 3 days to obtain the corresponding oxime, and
reducing the latter oxime by hydrogenating the oxime in the presence of a catalytic amount of a noble metal catalyst in an inert organic solvent to obtain the corresponding compound of formula I in which $R^4$, $R^5$ and $R^6$ are as defined herein, $R^1$ is hydrogen, $R^2$ and $R^3$ together are oxo, $R^7$ is hydrogen and $R^8$ is amino.

20. A method for treating hypertension in a mammal which comprises administering to said mammal an effective antihypertensive amount of a compound selected from those of formula I, or a therapeutically acceptable salt thereof, as claimed in claim 1.

21. A method for treating microbial infections in a mammal which comprises administering to said mammal an effective antimicrobial amount of a compound selected from those of formula I, or a therapeutically acceptable salt thereof, as claimed in claim 1.

22. A pharmaceutical composition having antihypertensive activity comprising a therapeutically effective amount of a compound of claim 1, and a pharmaceutically acceptable carrier.

23. The process as claimed in claim 17 which further comprises:
reacting said compound of formula V in which $R^4$, $R^5$ and $R^6$ are as defined therein with a lower alkyl or phenyl magnesium halide wherein the halogen is selected from chlorine, bromine or iodine in a solvent selected from ether or tetrahydrofuran for a time of from 5 minutes to six hours at a temperature of from $-25°$ C to the boiling point of the reaction mixture to obtain the corresponding compound of formula I in which $R^4$, $R^5$ and $R^6$ are as defined herein, $R^2$ and $R^3$ together are oxo, $R^7$ is hydroxy and $R^8$ is lower alkyl or phenyl.

24. The process as claimed in claim 23 which further comprises:
reducing said last named compound of formula I in which $R^1$, $R^2$, $R^3$, $R^4$, $R^6$, $R^7$ and $R^8$ are as defined therein and $R^5$ is lower alkyl with a complex metal hydride in a solvent selected from diethyl ether, dioxane, tetrahydrofuran, 1,2-dimethoxyethane for a time of from 2–30 hours at a temperature of from 60° C to the boiling point of the reaction mixture to obtain the corresponding compound of formula I in which $R^1$, $R^2$ and $R^3$ are hydrogen; $R^4$ and $R^6$ are as defined herein; $R^5$ is lower alkyl; $R^7$ is hydrogen and $R^8$ is lower alkyl or phenyl.

25. The process of claim 24 which further comprises:
acylating said last named compound of formula I with a halo(lower)alkanolyl halide of the formula (Halogen)-$CO(CH_2)_n$-Halogen) in the presence of a base selected from the alkali metal carbonates and hydroxides in a solvent inert to said acylation at a temperature from about 0° C to about 30° C for a period of about 30 minutes to about ten hours; wherein n is an integer from 1 to 4 and the halogens are selected from bromine, iodine or chlorine to obtain the corresponding haloalkanoylate intermediate of formula I in which $R^1$ is $CO(CH_2)_n$-Halogen, and;
aminating the latter compound with a molar excess of an amine of formula $HNR^9R^{10}$ in which $R^9$ and $R^{10}$ each are hydrogen or lower alkyl in an inert organic solvent at 0° C to 100° C for a period of 30 minutes to 20 hours to obtain the corresponding compound of formula I in which $R^1$ is $CO(CH_2)_nNR^9R^{10}$ wherein n, $R^9$ and $R^{10}$ are as defined herein, $R^2$ and $R^3$ are hydrogen, $R^4$ and $R^6$ are as defined herein; $R^5$ is lower alkyl; $R^7$ is hydroxy and $R^8$ is lower alkyl or phenyl.

26. The process of claim 25 which further comprises:
reducing said last named compound of formula I with a complex metal hydride in a nonhydroxylic solvent selected from diethyl ether, dioxane, tetrahydrofuran, 1,2-dimethoxyethane for a time of from 2-30 hours at a temperature of from 60° C to the boiling point of the reaction mixture to obtain the corresponding compound of formula I in which $R^1$ is $CH_2(CH_2)_nNR^9R^{10}$ wherein n, $R^9$ and $R^{10}$ are as defined herein, $R^2$ and $R^3$ are hydrogen; $R^4$ and $R^6$ are as defined herein; $R^5$ is lower alkyl; $R^7$ is hydroxy and $R^8$ is lower alkyl or phenyl.

27. The process of claim 17 which further comprises:
reducing said compound of formula V in which $R^4$ and $R^6$ are as defined therein and $R^5$ is lower alkyl with a complex metal hydride in a nonhydroxylic solvent selected from diethyl ether, dioxane, tetrahydrofuran, 1,2-dimethoxyethane for a time of from 2–30 hours at a temperature of from 60° C to the boiling of the reaction mixture to obtain the corresponding compound of formula 1 in which $R^4$ and $R^6$ are as defined herein; $R^1$, $R^2$, $R^3$ and $R^8$ are hydrogen; $R^5$ is lower alkyl and $R^7$ is hydroxy.

28. The process of claim 27 which further comprises:
acylating said last named compound of formula 1 with a halo(lower)alkanoyl halide of the formula (Halogen)-$CO(CH_2)_n$-(Halogen) in the presence of a base selected from the alkali metal carbonates and hydroxides in a solvent inert to said acylation at a temperature from about 0° C to about 30° C for a period of about 30 minutes to about 10 hours; wherein n is an integer from 1 to 4 and the halogens are selected from bromine, iodine or chlorine to obtain the corresponding haloalkanoylate intermediate of formula 1 in which $R^1$ is $CO(CH_2)_n$-Halogen, and;
aminating the latter compound with a molar excess of an amine of formula $HNR^9R^{10}$ in which $R^9$ and $R^{10}$ each are hydrogen or lower alkyl in an inert organic solvent at 0° C to 100° C for a period of 30 minutes to 20 hours to obtain the corresponding compound of formula I in which $R^1$ is $CO(CH_2)_nNR^9R^{10}$ are as defined herein, $R^2$ and $R^3$ are hydrogen, $R^4$ and $R^6$ are as defined herein; $R^5$ is lower alkyl and $R^7$ is hydroxy.

29. The process of claim 28 which further comprises:
reducing said last named compound of formula 1 with a complex metal hydride in a nonhydroxylic solvent selected from diethyl ether, dioxane, tetrahydrofuran, 1,2-dimethoxyethane for a time of from 2-30 hours at a temperature of from 60° C to the boiling point of the reaction mixture to obtain the corresponding compound of formula in which $R^1$ is $CH_2(CH_2)_nNR^9R^{10}$ wherein n, $R^9$ and $R^{10}$ are as defined herein, $R^2$ and $R^3$ are hydrogen; $R^4$ and $R^6$ are as defined herein; $R^5$ is lower alkyl and $R^7$ is hydroxy.

30. A pharmaceutical composition having antimicrobial activity comprising a therapeutically effective amount of a compound of claim 1, and a pharmaceutically acceptable carrier.

31. A composition having antimicrobial activity comprising an antimicrobially effective amount of a compound of claim 1, and a carrier.